United States Patent [19]

Hoffman

[11] 4,196,520
[45] Apr. 8, 1980

[54] METHOD OF REMOVING A CROWN FROM A TOOTH

[76] Inventor: Leo J. Hoffman, Gateways Executive Mall, 800 Woodbury Rd., Woodbury, N.Y. 11797

[21] Appl. No.: 21,999

[22] Filed: Mar. 19, 1979

[51] Int. Cl.² .............................................. A61C 3/16
[52] U.S. Cl. .................................... 433/218; 433/153
[58] Field of Search ................... 32/41, 42, 43, 44, 45, 32/7, 12

[56] References Cited
U.S. PATENT DOCUMENTS 1,176,548   3/1916   Harpin ...................................... 32/45

FOREIGN PATENT DOCUMENTS 498915   2/1952   Italy ............................................. 32/43

Primary Examiner—Robert Peshock
Attorney, Agent, or Firm—Bauer & Amer

[57] ABSTRACT

Instead of prying the crown in the direction opposite to the direction in which it was forced onto its cooperating support tooth, the within crown-removal method calls for initially preparing the crown with a vertically oriented cleave, and then projecting crown-spreading members into the cleave so as to produce an enlargement thereof in its circumferential dimension, with the result that the crown is correspondingly expanded circumferentially and thus is readily disengaged from the tooth.

3 Claims, 11 Drawing Figures

METHOD OF REMOVING A CROWN FROM A TOOTH

The present invention relates generally to improvements in crown-removal techniques, and more particularly to a method of disengaging a previously cemented crown from its support tooth that is characterized by being easily implemented, and thus beneficial to the patient and dentist by virtue of its safety in operation while offering minimal discomfort.

The approach of prior art crown-removal techniques is to pry or work the crown loose of its support tooth. Thus, as exemplified by the method described in U.S. Pat. No. 1,177,706, the crown is progressively rocked off of its support tooth in the direction opposite to that in which it was forced in covering relation over the tooth. No matter how a dentist may practice this method with care and concern for the comfort of the patient, the force that necessarily must be applied to pry or move the crown relative to the tooth must also, of necessity, manifest a counteracting response in the patient which, for most individuals, is accompanied by feelings of anxiety and discomfort.

Broadly, it is an object of the present invention to cause removal of a crown in accordance with method aspects that effectively overcome the foregoing and other shortcomings of the prior art. Specifically, it is an object to disengage the crown without progressive prying movements therein relative to its support tooth, and thus without exerting any force or pressure on the support tooth. In practice, it has been found that the patient typically remains comfortable and without any noticeable anxiety while the dentist, usually able to perform the within method with significant facility and dispatch, is readily able to remove the crown.

The within method of removing a crown from a tooth demonstrating objects and advantages of the present invention is necessarily, of course, practiced with an instrument effective to provide the necessary mechanical advantage in the applied force to overcome the attachment between the crown and the tooth. Such instrument recommended for practicing the within method is one characterized by having first and second elongated body members terminating in opposite proximal and distal ends, means for mounting said first body member in sliding relation to said second body member, a positioning handle on said proximal end of said second body member, and a pair of laterally extending crown-separating tips on the distal end of each said member in an initial position of aligned relation to each other and movable therefrom into spaced-apart relation upon sliding movement of said first body member. The within method of removing a crown while using said aforesaid instrument includes an initial step of cutting a vertically oriented cleave in the buccal or lingual aspect of the crown requiring removal and then projecting the aligned crown-spreading tips of the instrument into the cleave. To assist in maintaining the aligned tips within the cleave, it is necessary only that a slight pressure be applied at the handle which effectively applies a turning moment on said instrument. While this slight pressure is maintained, the dentist actuates the instrument first body member through sliding movement to produce the spread-apart condition in the tips and this results in the cleave enlarging circumferentially to correspondingly cause a circumferential enlargement of the crown in relation to its support tooth, and thus the disengagement thereof from the tooth.

The above brief description, as well as further objects, features and advantages of the present invention, will be more fully appreciated by reference to the following description of the within inventive method, when taken in conjunction with the accompanying drawings, wherein.

Figure 4:
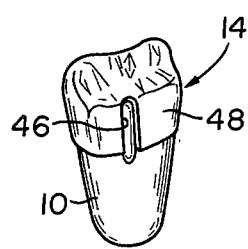
FIG. 4 is a perspective view illustrating one preferred manner in which a crown is prepared for removal in accordance with the present invention.
Figure 5:
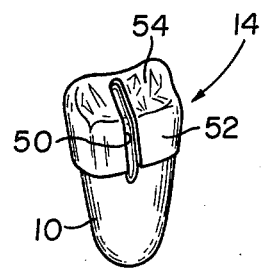
Figure 6:
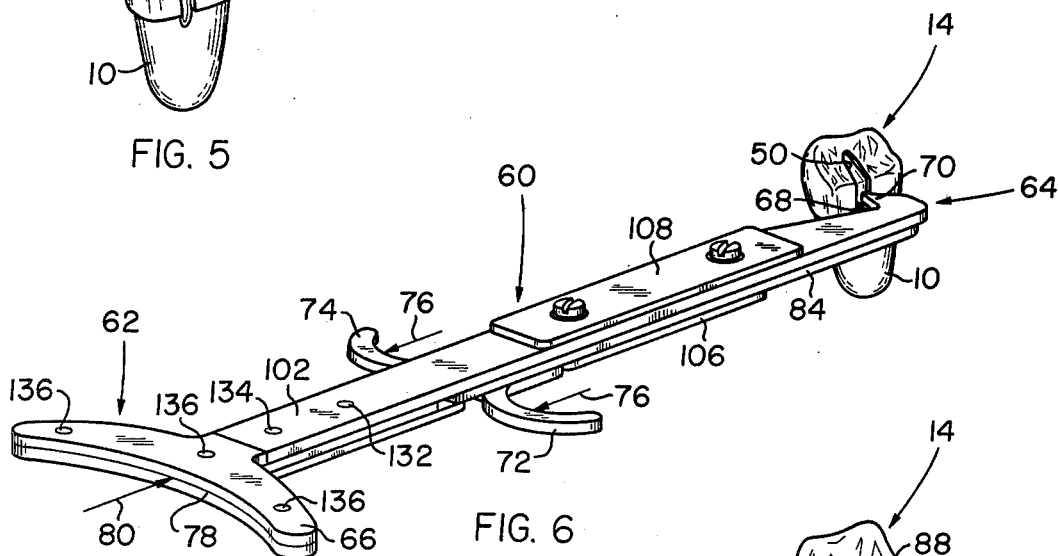
Figure 7:
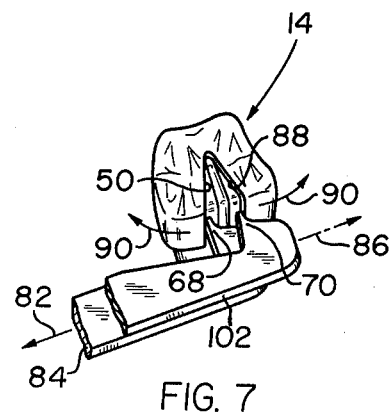
Figure 8:
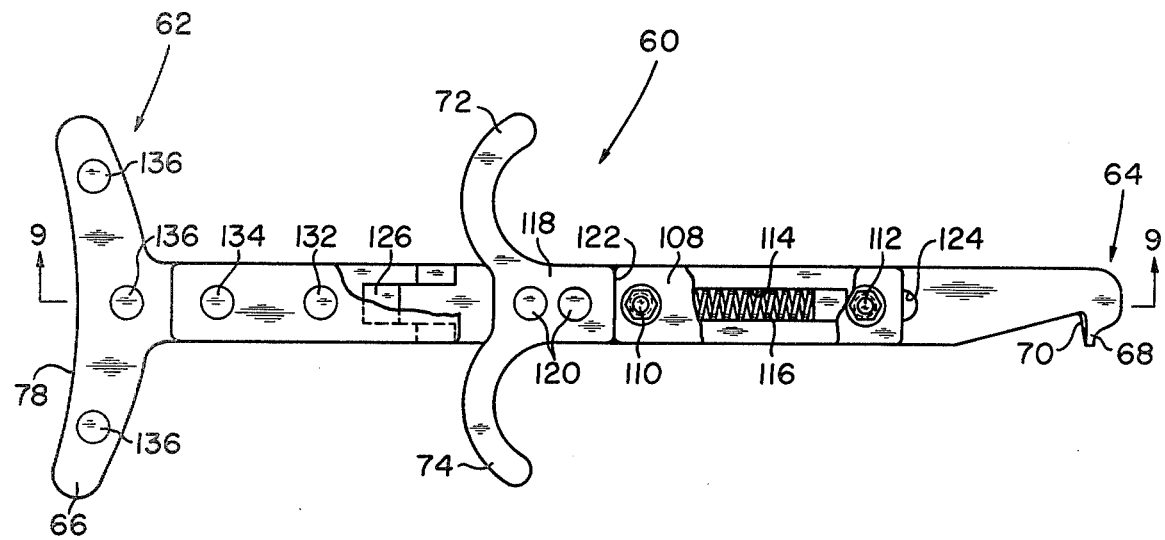
Figure 9:
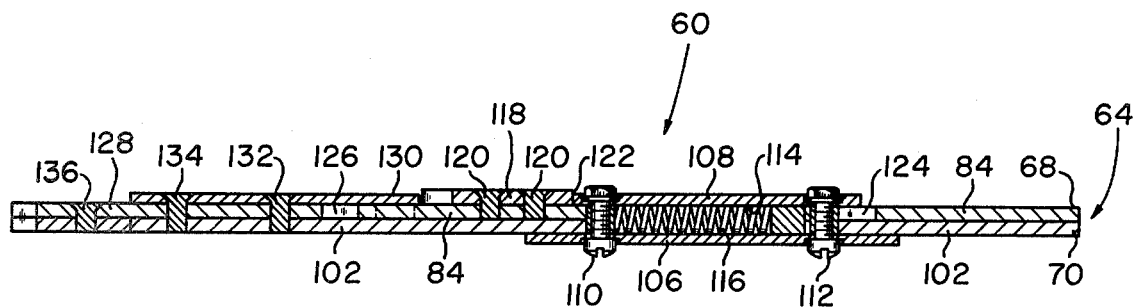
Figure 10:
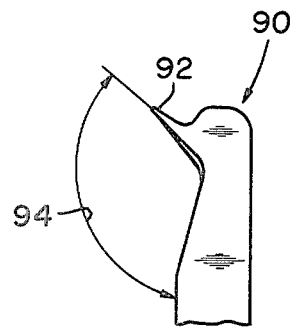
Figure 11:
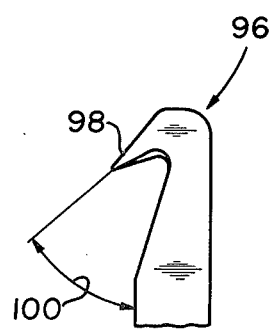

FIG. 5, like FIG. 4, is a perspective view of a crown, but illustrating an alternative way of preparing the crown for removal using the method of the present invention;

The remaining figures illustrate method aspects of the within invention as well as a preferred construction in an instrument that is particularly suitable for practicing the within invention. More particularly, FIG. 6 is a perspective view of an instrument recommended for use in practicing the within crown-removing method, said instrument being illustrated in its position initiating the crown-removal method hereof;

FIG. 7 is a partial perspective view illustrating how the instrument is actuated into an operational mode which results in disengagement of the crown from the tooth;

The remaining figures illustrate further structural details of the instrument. More particularly, FIG. 8 is a plan view of the instrument, as seen from the reverse side as illustrated in FIG. 6, in which several external portions are broken away to illustrate internal structural features;

FIG. 9 is a longitudinal sectional view, taken along line 9—9 of FIG. 8, illustrating further structural details; and FIGS. 10 and 11 are partial plan views of two alternative constructions for the distal end of the instrument.

Figure 3:
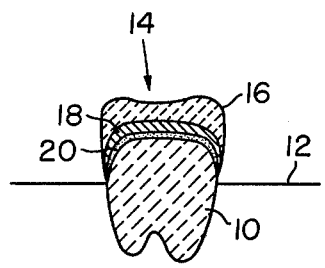
FIG. 3 illustrates in cross-section the conventional manner in which a tooth is fitted with a crown.

Since the present invention is concerned with facilitating the removal of a cemented crown from a tooth, it is helpful to refer first to the cross-sectional view of a crown in position on a tooth illustrated in FIG. 3. This figure, it will be understood, illustrates in somewhat simplified fashion a tooth 10 appropriately rooted in bone 12 and extending beyond the gumline and having on the upper extending portion thereof a crown construction 14 previously applied for well understood reasons, such as for treatment, or to satisfy a need for major esthetic improvement, as well as possibly for restoration of function and comfort. In any event, crown construction 14 includes the crown body 16 per se, usually of porcelain construction material, a metal coping 18, usually gold but which also can be a non-precious metal, and a layer of an appropriate cement 20 shown in a somewhat exaggerated thickness in FIG. 3 that is effective to maintain the gold coping 18 in place. In most instances the cement 20 has a recognizable white or yellow color and this is helpful in the preparation of the crown for removal, as will be more particularly described in detail in connection with FIGS. 4 and 5.

Figure 1:
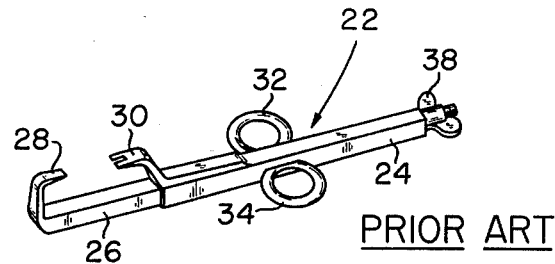
FIG. 1 is a perspective view of an exemplary prior art instrument for removing a crown of a tooth.
Figure 2:
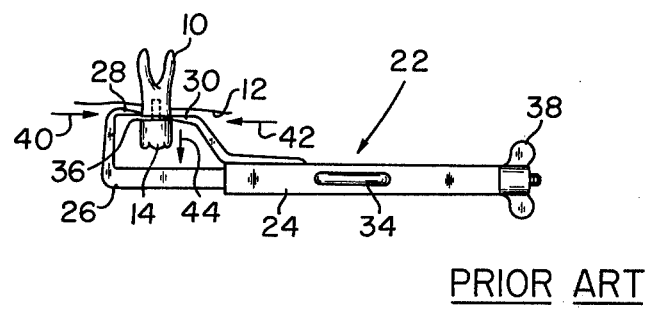
FIG. 2 illustrates the prior art method of removing said crown using the instrument of FIG. 1.

Prior to the referred to discussion, however, the within inventive contribution can be better appreciated by first making note of the salient features of the current or prior art methods of removing crowns. Since each crown is fitted firmly on its support tooth, for obvious reasons, any crown-removal method cannot be achieved or practiced without the use of an instrument that is capable of prying the crown loose from the tooth without rendering pain to the patient or damage to the underlying tooth. Thus to understand any prior art crown-removal method, it is also necessary to make reference to, and to understand, the operational mode of the instrument used in the practice of the method. With the providing of such understanding in mind, reference is therefore made to FIGS. 1 and 2 which respectively illustrate an exemplary prior art instrument, generally designated 22, and the manner in which such instrument is used in prying a crown 14 off of a support tooth 10. As understood, and also as is described in prior U.S. Pat. No. 1,177,706, instrument 22 includes a housing 24 for a slidably disposed body 26. On the housing and body 24, 26, respectively, are facing wedges 28 and 30. In use, the instrument is held in one hand by the finger grips 32 and 34 with the wedges 28 and 30 on opposite sides thereof, and thus in position to be projected or inserted within a horizontally oriented cleave 36 appropriately cut, as with a cylindrical diamond or burr, at the base of the crown 14 and the tooth 10, all as is clearly illustrated in FIG. 2.

From the position as just noted, the user, using his other hand, then tightens up on the thumb nut 38 which results in wedge 28 being urged through movement 40 into the cleave 36. The other wedge 30 is positioned in the cleave 36 as the result of positioning movements 42. The combined result of the movements 40 and 42 of the respective wedges 28 and 30 into the cleave 36 is to force the crown 14 off of the portion of tooth 10 which extends beyond the gumline 12. It should be noted, however, that this dislodging movment is in the direction 44, a direction which is lengthwise of the tooth. Direction 44 is also the reverse of the direction in which the crown is initially forced onto the tooth.

Underlying the present invention is the recognition that undesirable frictional resistance is encountered when the crown 14 is attempted to be urged through movement 44 off of its support tooth 10, and that therefore any crown-removing method requiring this direction of dislodging movement is therefore unnecessarily uncomfortable to the patient, difficult and more time consuming to implement, and could conceivably fracture all or any portion of the underlying tooth.

In contrast to the foregoing, the within inventive method results in the crown being removed in a greatly simplified and facilitated manner. To a great extent this is due, during removal of the crown, to causing circumferential expansion thereof rather than trying to pry the crown free of the tooth in a direction opposite to the direction in which it was originally placed in covering relation over the tooth. In practicing the within crown-removal method, the tooth having the crown may preferably be prepared in either of the two ways as illustrated in FIGS. 4 and 5. More particularly, as illustrated in FIG. 4, the crown 14 on tooth 10 is provided with a cleave 46 in the buccal surface 48 or, in some instances, in the lingual surface (not shown). This may be achieved with a cylinder diamond or burr, or other conventional manner. In FIG. 5 the crown 14 to be removed is similarly provided with a cleave 50, and as clearly illustrated in FIG. 5 cleave 50 is provided not only in the buccal surface 52 but also in the occlusal surface 54. In the preparation of both the teeth as illustrated in FIGS. 4 and 5, the user is guided in providing the proper depth to the respective cleaves 46 and 50 by noting when he has reached the white or yellow color of the underlying cement layer.

In the remaining description it will be assumed that the within inventive method is applied to the removal of the crown construction 14 from tooth 10 prepared with a cleave 50 as shown in FIG. 5. The method contemplates using an instrument 60 which as shown in FIG. 6 is characterized by a generally elongated body having opposite proximal and distal ends 62 and 64, respectively. Instrument 60 has an arcuate shaped handle 66 on the proximal end 62 thereof, and at the distal end 64 has two laterally extending crown-spreading tips 68 and 70, respectively. Upon progressive examination of FIGS. 6 and 7, it will be noted that the initial position of the tips 68 and 70 is one in which they are in aligned relation to each other. As such, and as clearly illustrated in FIG. 6, the tips 68, 70 are readily positioned within the cleave 50.

To facilitate providing the tips 68, 70 with their projected position within the cleave 50 and to hold these tips in place while the crown-removing method is practiced, instrument 60 has a pair of laterally extending finger grips 72 and 74 which promote the recommended manner in which instrument 60 is to be held and manipulated during the within crown-removal method. More particularly, and as illustrated in FIG. 6, the arrows 76 signify the establishment of finger engagement with the grips 72 and 74 and simultaneously therewith the pushing of the instrument 60 firmly into the palm of the user so that the rear surface 78 of the handle 66 abuts firmly, as signified by the arrow 80, against the user's palm of the same hand which of course provides him with finger engagement with the finger grips 72 and 74. In other words, as represented by the facing arrows 76 and 80, instrument 60 is firmly engaged at the proximal end 62 by forces exerted in the opposite directions noted. Also, finger engagement with the grips 72 and 74 readily enables the user, by merely drawing back on the finger grips, to produce relative movement between the tips 68 and 70 at the distal end 64 of the instrument, all as will be described in detail subsequently. During finger manipulation of the grips 72 and 74, as just noted, the user is readily able to apply pressure with his palm in the direction 80 against the handle 66 so as to apply a turning moment to the instrument 60 which results in the distal end 64 thereof being urged in the direction of the tooth 10. In this way the initially aligned tips 68 and 70 are effectively held in position within the cleave 50.

Referring now to FIG. 7, the drawing back on the finger grips 72 and 74 will be understood to result in actual sliding movement 82 in that body member 84 which has the tip 68 formed on the distal end thereof. The other tip 70 is stationary and as signified by arrow 86, it is pressed against the far edge 88 which bounds the cleave 60 by the previously noted palm pressure 80. The result of the spread-apart position that is assumed by the tips 68 and 70 is of course enlargement of the cleave 50 and thus circumferential enlargement, as represented by the arrows 90, of the crown construction 14. As may be readily appreciated, the enlarged size assumed by the crown construction 14 readily results in its being disengaged from the supporting tooth 10 which, of course, remains unchanged in size.

Before describing the construction of instrument 10 which provides the operational modes thereof as just described, it is perhaps convenient at this point to note the alternative embodiment that may be provided at the distal end of the instrument as illustrated in FIGS. 10 and 11. More particularly, as illustrated in FIG. 10, another embodiment of instrument 60 might be comprised of a distal end 90 in which the aligned tips, individually and collectively designated 92, are not oriented 90 degrees of the longitudinal dimension of the instrument but instead subtend an obtuse angle 94. In another contemplated embodiment as illustrated in FIG. 11, the instrument distal end 96 has aligned tips 98 which subtend an acute angle 100. From the two embodiments 90 and 96 just described it should be readily appreciated that tips subtending any other selected angle can also be embodied in the distal end of the instrument. The location of the tooth having the crown requiring removal dictates the angle that is selected for the tips. In practice, good results have been achieved in removing crowns using the within inventive method from all locations of teeth with the perpendicularly extending tips 68 and 70 of instrument 60. Some practitioners, however, may prefer using the FIG. 11 embodiment to remove crowns from posterior teeth, while the FIG. 10 embodiment may be found easier to manipulate for anterior teeth.

A preferred embodiment for instrument 60 is shown in FIGS. 6, 8 and 9, to which figures reference should now be made. Instrument 60 is capable of being used whether the tooth is located in the right or the left-hand portion of the patient's mouth, it being simply a matter of turning the instrument 180 degrees. This has been done in illustrating the instrument 60 in FIGS. 6 and 8.

Instrument 60 is comprised of a first body member 102 which, of the two body members, is the one that is stationary and terminates at distal end 64 with laterally extending tip 70. Disposed in sliding relation to body member 102, at least at the distal end 64 of the instrument, is previously noted body member 84. It is of course on the distal end of body menber 84 that the instrument is provided with the movable laterally extending tip 68. As is perhaps best illustrated in the cross-sectional view of FIG. 9, the two body members 102 and 84 are held together between two plates 106 and 108 by two screw connectors 110 and 112. The plates 106 and 108 also function as covers for a compartment 114 formed centrally of the body members 102 and 104. Disposed in compartment 114 is a compression spring 116 which normally holds the tips 68 and 70 in their initial aligned relation. More particularly, the hand grips 72 and 74 are part of the member 118 which is riveted, as at 120, to a rearwardly disposed portion of body member 84. A preferred effective way of achieving the aligned relation between the tips 68 and 70 is thus to arrange for the abutment of the front edge 122 of member 118 against the rearwardly disposed edge of plate 108, making sure that such abutment results in the desired alignment between the tips 68 and 70. When drawing back on the finger grips 72 and 74, however, body member 84 is slidable relative to the stationary body 102 to the extent of the clearances 124 and 126 provided respectively fore and aft of the medial portion of body member 84.

As is perhaps best illustrated in FIG. 9, cooperating with the rearwardly disposed portion of the stationary body member 102 is an extension 128 of the body member 84, said extension 128 and the rearwardly disposed portion of body member 102 cooperating to define the handle 66 at the proximal end 62 of the instrument. To connect the rearwardly disposed portion of body member 84 or, more particularly, the extension 128 thereof, to the first body member 102, use is made of a connecting plate 130 and the rivets 132, 134. Completing the assembly of the handle 66 are additional rivets 136.

To reiterate briefly the operational mode of instrument 60 as just described, spring 116 is effective in urging the finger piece body 118, or at least edge 122 thereof, against plate 108 and, as a consequence, is effective in providing an aligned relation between the tips 68 and 70. When the user, however, draws back on the finger grips 72 and 74, body member 84 is urged through sliding movement in relation to body member 102 to the extent of the clearance 124 in relation to the stationary screw 112 as well as to the extent of clearance 126 in relation to the stationarily mounted extension 128 of the body member 104, both said clearances 124, 126 being approximately the same size. This sliding movement is against the resistance of spring 116. Thus, when the finger grips 72 and 74 are released, spring 116 is effective in restoring the initial alignment of the tips 68 and 70. As just described, therefore, instrument 60 has an operational mode which is effective for practicing the within inventive method of removing crowns, in that the crown is removed by being circumferentially enlarged during which there is disengagement of the crown from the supporting tooth. This is in contrast to prior art methods of crown removal, exemplified by FIGS. 1 and 2, in which the crown is removed by being pried free of the supporting tooth in a direction that is opposite to, or in reverse to, the direction in which it was placed in covering relation over the tooth.

A latitude of modification, change and substitution is intended in the foregoing disclosure, and in some instances some method aspects of the invention will be employed without a corresponding use of other aspects. Accordingly, it is appropriate that the appended claims be construed broadly and in a manner consistent with the spirit and scope of the invention herein.

What is claimed is:

1. A method of removing a crown from a tooth using an instrument characterized by having first and second elongated body members terminating in opposite proximal and distal ends, means for mounting said first body member in sliding relation to said second body member, a positioning handle on said proximal end of said second body member, and a pair of laterally extending crown-separating tips on the distal end of each said member in an initial position of aligned relation to each other and movable therefrom into spaced-apart relation upon sliding movement of said first body member, said method of removing a crown while using said aforesaid instrument comprising the steps of forming a vertically oriented cleave in a crown disposed in covering relation over a tooth, positioning said aligned crown-spreading tips of said instrument in said cleave, maintaining said positioned aligned tips within said cleave under slight pressure by applying a turning moment on said instrument at said handle thereof, and while maintaining said slight pressure as aforesaid actuating said instrument first body member through sliding movement to produce said spread-apart condition in said tips, whereby said cleave is enlarged circumferentially to correspondingly cause a circumferential enlargement of said crown in relation to said tooth so as to promote the disengagement thereof from said tooth.

2. The method of removing a crown as defined in claim 1 while using the instrument also as defined in claim 1, wherein said first body member has laterally extending finger grips and with the same hand used to apply said slight pressure at said handle thereof finger engagement is also made with said finger grips preparatory to drawing back on said first body member, whereby said first body member is urged through said sliding movement without letting up on said turning moment being simultaneously applied thereto.

3. The method of removing a crown as defined in claim 2 while using the instrument also as defined in claim 2, wherein said positioning handle is of an arcuate shape and in use is held by said finger engagement with said finger grips against the user's palm, whereby movements of the user's palm and fingers have an effective manipulative effect in the positioning and actuating of said instrument during removal of a crown.

* * * * *